US006377058B1

(12) United States Patent
Pemrick

(10) Patent No.: US 6,377,058 B1
(45) Date of Patent: Apr. 23, 2002

(54) DEVICE AND METHOD FOR MEASURING HAY BALE MOISTURE

(75) Inventor: Peter Pemrick, Chanhassen, MN (US)

(73) Assignee: Harvest TEC, Inc., Hudson, WI (US)

( * ) Notice: Subject to any disclaimer, the term of this patent is extended or adjusted under 35 U.S.C. 154(b) by 0 days.

(21) Appl. No.: 09/457,810

(22) Filed: Dec. 9, 1999

(51) Int. Cl.⁷ ............................................. G01N 27/12
(52) U.S. Cl. ...................... 324/695; 324/694; 324/696; 324/701; 56/10.2 B; 73/73
(58) Field of Search ................................. 324/693, 694, 324/695, 696, 701, 713, 715, 717, 722, 724; 56/10.2 B; 73/73

(56) References Cited

U.S. PATENT DOCUMENTS

| 4,868,491 A | * | 9/1989 | Black .......................... 324/694 |
| 4,929,904 A | * | 5/1990 | Bohman et al. ............. 324/696 |
| 6,088,657 A | * | 7/2000 | McMahon ............... 324/694 X |

\* cited by examiner

*Primary Examiner*—Glenn W. Brown
(74) *Attorney, Agent, or Firm*—Robert A. Elwell

(57) ABSTRACT

A device for sensing moisture in moving hay bales has a pair of star-shaped wheels situated to have points penetrate into the bale and be driven by the bale. The points establish electrode surfaces within the bale between which resistivity or conductivity of an electrical current may be measured and scaled to moisture content of the hay of the bale.

16 Claims, 1 Drawing Sheet

DEVICE AND METHOD FOR MEASURING HAY BALE MOISTURE

BACKGROUND OF THE INVENTION

FIELD OF INVENTION

The present invention relates to devices and methods for measuring moisture in hay and similar crops and, in particular, the present invention relates to devices and methods for measuring moisture in hay during a baling process.

Hay, a major crop for feeding livestock, is commonly prepared by cutting alfalfa or grass stems near the ground, allowing the newly cut material to air dry on the ground for a period of time, and then subsequently harvested by a hay baler. One type of hay balers in common use functions to package hay into a compressed unit, often a rectangular package, by packing the crop into a chute, tying twine around the bale and then discharging the finished bale. Since hay will spoil in a bale with a moisture content above about 18 percent (weight per weight), knowing the moisture of the hay being baled is important. Moisture content of the hay, particularly while drying on the ground prior to baling, is subject to rapid changes as wind and sun can quickly remove moisture from the crop or as rain or dew can quickly add moisture to the crop. One practical method of determining hay moisture would employ a test instrument that provides accurate and rapid readings in the field to help determine the suitability of the crop to be baled.

Electronic moisture testers are in common use in the production of hay to provide meaningful and quick references to the moisture of the hay. The common forms of electronic testers include hand held instruments with a probe to insert into the hay baler, a portable canister unit to fill with the hay to be sampled, or a two point sensor mounted on the baler with the sensors connected to a readout module. Typically, a readout module is located in the cab of the tractor pulling the baler. All electronic testing units in common use currently employ direct current power at a low level, usually around five volts, to send a signal out through one electrode in contact with the hay bale being measured. The most common type of tester then reads the amount of voltage reaching a second electrode in contact with the bale. This reading is directly related to moisture content of the hay and is scaled in a readout to indicate the moisture content of the crop. A variation on this method is to read the impedance of voltage sent through one electrode. Such impedance is also related to the moisture content of the crop and may therefore be scaled and read as a moisture number by an instrument connected to the electrode.

Recently, the most popular method of reading electronic moisture has been to employ a sensor using the two electrode points sensors mounted on the interior pathway of a hay baler. This type of sensor uses one point as the voltage source electrode and the other point as the voltage receiving electrode. Normally, both electrodes are mounted along the pathway of the baler using a single non-conductive pad that isolates each bolt from the other and from other conductive materials in the baler. As hay passes by the non-conductive pad with two electrodes, voltage is conducted from one electrode to the other electrode. As the moisture increases in the hay, conductivity increases giving a signal which can then be scaled and read in the cab of the tractor as the baler is operated.

A sensor arrangement with a single non-conductive pad and two electrodes might be expected to provide a satisfactory method of sensing hay moisture. Investigative field tests were carried out to assess performance of such prior art sensors. Specifically, a variety of hay bales with different moisture content were tested using less convenient, but more dependable and accepted analytical moisture determination methods and comparing such analytical moisture tests to the readings generated by a conventional prior art sensor with two electrode mounted upon a single pad with the following surprising results:

|        | ELECTRONIC MOISTURE | LAB MOISTURE |
|--------|---------------------|--------------|
| BALE 1 | 17.4%               | 13.6%        |
| BALE 2 | 28.5%               | 16.9%        |
| BALE 3 | 15.9%               | 11.1%        |
| BALE 4 | 26.0%               | 18.4%        |
| BALE 5 | 32.4%               | 19.1%        |
| BALE 6 | 39.0%               | 22.9%        |

Clearly, the results show that the tested prior art sensor was unacceptable.

The observed short-comings of a sensor with a single non-conductive pad bearing two electrode were considered and attributed by the present inventor to four different effects which are detrimental to reliable hay moisture measurement. First, the observed conductivity measurement from the pad with two electrodes arrangement is effected by the amount of pressure of the hay against the non-conductive pad and its electrodes. Specifically, in practice, the single non-conductive pad with two electrodes generates higher conductivity readings at higher hay pressures. The higher conductivity readings can be misinterpreted as higher moisture content percentages. Accuracy of the moisture reading is therefore significantly effected and compromised by changes in bale compression pressure. Second, accuracy is also adversely effected by static electricity build up caused by hay rubbing against the two electrodes and the associated non-conductive pad. Third, accuracy is also effected by any organic residue left on the electrodes from the hay going past the non-conductive pad and two electrodes. Fourth, accuracy is also subject to be adversely effected by the location of the pad relative to the passing bale when the single surface region of contacting the electrodes is not representative of an entire bale's hay content.

The prior art sensor system, employing a non-conductive pad and two electrodes is undependable for hay moisture measurement. A better moisture measurement device and method which addresses the deficiencies of sensors with a single non-conductive pad and two electrodes has now been invented.

BRIEF DESCRIPTION OF THE FIGURE.

(In FIG. 1, only portions of a conventional baler associated with a hay pathway through the baler are shown for clarity.)

Figure 1:
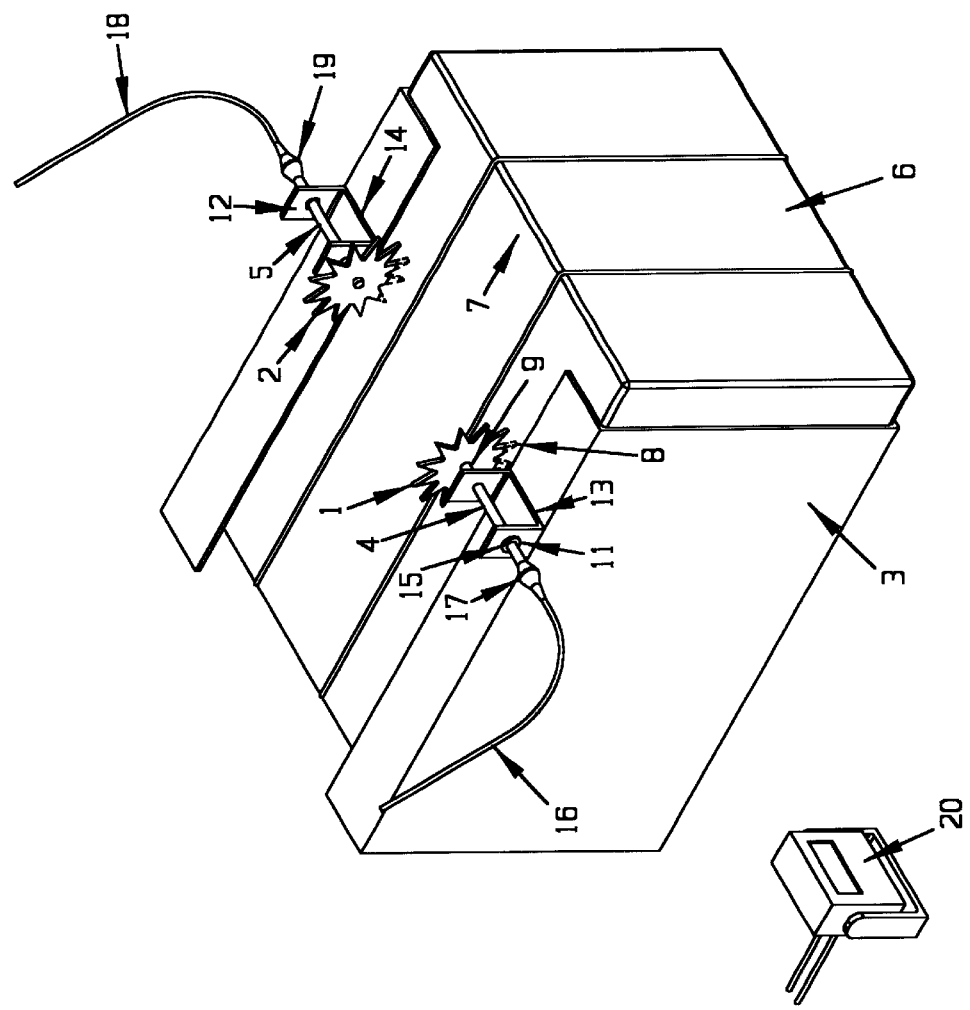
FIG. 1 is a schematic representation of moving compressed hay progressing, for example moving through a baling apparatus, and being measured for moisture content according to an embodiment of the present invention.

SUMMARY OF THE INVENTION.

The present invention, in a first embodiment, is a device including two star-shaped wheels. Each of these star-shaped wheels has a plurality of points and each of the star-shaped wheels is mounted on a hay baler, such that points of the star-shaped wheels rotatably protrude into hay being baled by and progressing through the baler. In the case of rectangular block bales, the points preferably penetrate between parallel stems of the hay compressed into the bale form and are driven to rotate by the moving hay. The star-shaped wheels have a non-conductive arrangement electrically isolating the two star-shaped wheels from each other and from the metal framing of the baler on which they are mounted. Additionally, the device includes means to transmit direct current voltage to one of the two star-shaped wheels and means to transmit direct current voltage reaching the other of the two star-shaped wheel through hay being baled by and progressing through the baler. Preferably, these transmission means would be insulated wires but might alternatively include printed circuitry. The transmitted current is sent to a readout box. The box includes electrical circuitry to scale the voltage returning through the second wheel into a moisture reading. The readout box then can display the moisture reading. The reading can also be used to control other processes or provide alternative signals, such as sound or visual signals, such as a flashing light.

The hay baler preferably has a conductive frame, and the device has a non-conductive means to electrically isolate, preferably a non-conductive pad electrically separating a mounting bracket carrying one of the two star-shaped wheels from the conductive frame of the baler. The device also preferably has other non-conductive means to electrically isolate, such as a non-conductive bearing electrically separating one of the star-shaped wheels from the conductive frame of the baler. The means to transmit direct current voltage to one of the star-shaped wheels and the means of transmitting voltage from the other of the star-shaped wheels may include conductive swivels providing rotatable electrical connections to each of the two star-shaped wheels.

Preferably, the circuitry is such that the readout is scaled to read 10% (wt/wt) moisture for voltage readings returning between 9.91 and 9.78, 12% for voltage readings returning between 9.77 and 9.60, 14% for voltage readings returning between 9.59 and 8.00, 16% for voltage readings returning between 7.99 and 7.00, 18% for voltage readings returning between 6.99 and 5.50, 20% for voltage readings returning between 5.49 and 4.00, 22% for voltage readings returning between 3.99 and 2.75, 24% for voltage readings returning between 2.74 and 2.00, 26% for voltage readings returning between 1.99 and 1.80, 28% for voltage readings returning between 1.79 and 1.60, 30% for voltage readings returning between 1.59 and 1.30, 32% for voltage readings returning between 1.29 and 1.20, and 34% for voltage readings returning between 1.19 and 1.10, when the supply voltage provides about 10 volts of direct current.

In another embodiment, the present invention is a sensor device for use in measuring moisture in moving compressed hay, such as hay being baled in a hay baler. The sensor includes two electrodes. The first electrode is a rotatable penetrating projection mounted adjacent to the moving compressed hay, such that the rotatable penetrating projection serves to provide a moving electrode surface situated within and in electrical contact with the moving compressed hay. The second electrode surface is situated in electrical contact with the moving compressed hay. The second electrode surface is spaced apart from the moving electrode surface provided by the rotatable penetrating projection. Moving compressed hay is interposed between the moving electrode surface and the second electrode surface. The interposed moving compressed hay provides an electrical path between the rotatable penetrating electrode surface and the second electrode surface. The conductive quality of the electrical path through the interposed moving compressed hay is a function of the moisture content of the interposed moving compressed hay.

Preferably, in the sensor device of the present invention, the second electrode surface also includes a second rotatable penetrating projection mounted adjacent to the moving compressed hay, such that the second rotatable penetrating projection serves to provide a second moving electrode surface situated within and in electrical contact with the moving compressed hay. The rotatable penetrating projection is preferably one of a plurality of penetrating projections carried by a star-shaped wheel, where the star-shaped wheel is rotatable about an axis situated transverse to the moving compressed hay and offset from the moving compressed hay. The star-shaped wheel is driven to rotate by the moving compressed hay acting upon the penetrating projections. Most preferably, the sensor device includes a pair of star-shaped wheels, with one of the star-shaped wheels providing the plurality of rotatable penetrating projections sequentially forming the first moving electrode surface and the second star-shaped wheel forming the second plurality of moving electrode surfaces, such that the electrode surfaces are not statically positioned relative to the moving compressed hay. Rather, the contact surface is being constantly renewed as the star points penetrate and rotate as they are driven by the stems of the compressed moving hay. Most preferably, the pair of star-shaped wheels are coaxial and are insulated from each other and from any conductive materials, such as the baler frame, which defines a pathway for the moving compressed hay. The sensor device is useful when the compressed moving hay is formed in a rectangular block mass type of bale. The rectangular bale has a linear path and has stems of the hay situated generally transverse to the linear path and parallel to the axis of rotation of the rotatable penetrating projection. The sensor device can also be used to measure moisture in a cylinder mass or round bale. Round bales are spirally wound about a cylinder axis, the cylinder axis situated parallel to and offset from the axis of rotation of the rotatable penetrating projection of the sensor device.

In another embodiment, the present invention is a method of measuring hay moisture within compressed moving hay. The method includes the steps of: providing a rotatable penetrating electrode surface within the moving compressed hay; providing a second electrode surface situated in electrical contact with the moving compressed hay, the second electrode surface spaced apart from the moving electrode surface provided by the rotatable penetrating projection, with moving compressed hay being interposed between the moving electrode surface and the second electrode surface. The interposed moving compressed hay provides an electrical path between the rotatable penetrating electrode surface and the second electrode surface. Electrical current, preferably D.C. current, most preferably at about 10 volts, is provided to the rotatable penetrating electrode surface. The current passing through the hay is detected at the second electrode and the fraction of electrical current conducted through the interposed compressed moving hay is a function of the moisture content of the hay. The detected current is converted into a moisture reading. The method is preferably carried out by providing star-shaped wheels, mounted on shafts offset from and transverse to the moving compressed hay. The method can be used on rectangular bales but may be adapted to measure moisture in a rotating round bale, as well. With round bales, a pair of star-shaped wheels may be brought into contact with the cylindrical surface of a rotating round bale.

DETAILED DESCRIPTION OF PREFERRED EMBODIMENTS

The present invention, in a first embodiment, is a device preferably adapted for mounting in or on hay balers to provide more accurate moisture and acceptably dependable readings than the reading provided by prior art sensors, such as the type tested above. In the embodiment shown in FIG. 1, two star-shaped wheels 1 and 2 are mounted to a conventional hay baler 3. The two star-shaped wheels 1 and 2 are mounted adjacent to a pathway followed by hay as it is formed into bales or as the formed bales are subsequently dispensed from the baler 3. The wheels 1 and 2 are attached to and carried by rotating shafts 4 and 5 so that they can freely rotate in a direction in line with the movement of the bale 6 as the baler 3 pushes bale 6 through the baler 3 in direction 7, i.e. along a bale pathway. Multiple points or projections 8 on the star wheel 1 extend, preferably from about one to about twenty inches, outward from the solid center portion 9 of the star wheel 1. The height or offset of the shafts 4 and 5 above bale path 7 is determined by the distance the points 8 extend out from the solid center 9, such that the points 8 of the star wheel 1 are protruding and penetrating into the bale 6 as it passes along the path 7. That is, the offset of the shafts 4 and 5 from the bale 6 progressing along path 7 is preferably not less than the radius of the solid center portion 9 and not more than the radius from the shaft 4 to the points 8. The movement of the bale 6 along path 7 causes the star wheels 1 and 2 to rotate, with shafts 4 and 5 also rotating. As the points 9 of the star wheel 1 enter and penetrate into the bale 6, they move downward through the compressed hay of the bale 6 providing contact with hay in that part of the bale 6. Note that the points 9 are in contact with hay which is interior to the surface of the bale 6. Similar points on star wheel 2 penetrate and contact hay, interior to the surface, of the bale 6 at a distance from star wheel 1.

Brackets 11 and 12 are located to hold the rotating shafts 4 and 5 in the offset position, as described above. These brackets 11 and 12 are mounted to the baler 3 by means of isolators 13 and 14 which are non-conductive, such that each star wheel 1 and 2 is electrically isolated from the baler 3 and electrically isolated from each other. In an alternative embodiment, the shafts 4 and 5 may be held by a bearing 15 which is constructed from non-conductive material, thereby isolating or insulating shafts 4 and 5 from the baler 3 and from each other. As shown in FIG. 1, both isolators 13 and 14 and non-conductive bearings 15 may be used together, or alternatively, to isolate or to increase electric isolation of the points 9 of one star wheel 1 from its alternate member star wheel 2. A wire 16 to conduct direct current voltage to star wheel 1 is attached to the rotating shaft 4 by means of a conductive swivel 17. Preferably, between about one-half and about eighty volts of direct current are transmitted to the wheel 1 so that direct current is applied to be conducted through the hay bale 6, and then conducted to the other wheel 2. Another wire 16 to conduct direct current voltage from star wheel 2 is attached to the rotating shaft 5 by means of a conductive swivel 19. Returning direct current voltage coming through wire 18 is read and scaled to a moisture reading which is displayed in box 20.

Scaling of the readout to represent the moisture of the hay has been done by running samples of hay through a typical baler equipped with the present invention and assigning values to voltage readings based on laboratory moisture tests of the hay samples.

EXAMPLE 1.

The values within box 20 were set as follows, based on supplying ten volts of direct current to star wheel 1. In this example, a typical hay baler apparatus was used. John Deere and New Holland are typical sources of such equipment. A pair of star wheels prepared from ¼ inch steel, (by stamping), and had 12 points, a solid center diameter of about 6 inches and the points extended to a diameter of about 10 inches. (Generally, points extending about 2–3 inches are preferred.) The wheels were mounted with an offset from bales progressing through the balers hay bale path, such that the points penetrated from about 1–3 inches into the bales. Laboratory moisture tests of the hay from the bales were performed. Samples were promptly taken and protected during transport and storage to avoid moisture changes.

| LAB MOISTURE CONTENT | VOLTAGE READING FROM WHEEL 2 |
| --- | --- |
| 10% | 9.91–9.78 |
| 12% | 9.77–9.60 |
| 14% | 9.59–8.00 |
| 16% | 7.99–7.00 |
| 18% | 6.99–5.50 |
| 20% | 5.49–4.00 |
| 22% | 3.99–2.75 |
| 24% | 2.74–2.00 |
| 26% | 1.99–1.80 |
| 28% | 1.79–1.60 |
| 30% | 1.59–1.30 |
| 32% | 1.29–1.20 |
| 34% | 1.19–1.10 |

These values were stored in a memory device included in 20 and assigned to the readout display as the values are read from star wheel 2. When a value below the arbitrarily assigned minimum value of 10% moisture was read, the display was set to read "low". When a value above the arbitrarily assigned maximum value of 40% is read, the display is set to read "high".

While the preferred embodiment involves spaced apart paired generally similar star wheels 1 and 2 which are arranged in an offset, generally coaxial configuration, and rotating, the invention, in another embodiment, may be carried out without a coaxial arrangement between shafts 4 and 5, but rather with shafts 4 and 5 parallel to, but offset from each other. In such an arrangement, the paired star wheels may lie in a single plane or two parallel but offset planes. In another embodiment, the star wheels need not be of generally identical dimensions, rather one might be large and one smaller. In another embodiment, the star wheels whether generally identical in dimension or not, need not have identical shaft offsets from the bale pathway. In yet another embodiment, the star wheels may have portions of their surfaces insulated, as long a conductive element rotatably penetrates into the compressed hay, and in an extreme embodiment, the star wheels may be discs without projecting points. However, in all such alternative embodiments, as well as the preferred embodiments, at least one electrically conductive point or projection or surface must rotatably penetrate into a mass of compressed hay which is progressing or moving and thereby provide a first electrical contact with the mass of compressed hay and additionally, there must be a second electrical contact, spaced apart from the first contact, with electrical current passing between the two contacts.

Although the present invention has been described with reference to preferred embodiments, workers skilled in the art will recognize that changes may be made in form and detail without departing from the spirit and scope of the invention.

What is claimed is:

1. A device comprising:
    a first star-shaped wheel and a second star-shaped wheel, each of the star-shaped wheels having points and each of the star-shaped wheels having means to mount the star-shaped wheel on a hay baler, such that points of each of the star-shaped wheels rotatably protrude into and are driven by hay being baled by and progressing through the hay baler;

non-conductive means to electrically isolate the two star-shaped wheels from each other and from the hay baler;

means to transmit direct current voltage to the first star-shaped wheel;

means to transmit direct current voltage reaching the second star-shaped wheel through hay being baled by and progressing through the hay baler, from the first star-shaped wheel;

means to scale the direct current voltage transmitted to the first wheel, through the hay, and then returning from the second wheel into a moisture reading; and, means for displaying the moisture reading at a readout box.

2. The device of claim 1, wherein the hay baler has a conductive frame, and wherein the non-conductive means to electrically isolate includes a non-conductive pad electrically separating a mounting bracket carrying one of the two star-shaped wheels from the conductive frame of the baler.

3. The device of claim 1, wherein the hay baler has a conductive frame, and wherein the non-conductive means to electrically isolate includes a non-conductive bearing electrically separating one of the star-shaped wheels from the conductive frame of the baler.

4. The device of claim 1, and wherein the means to transmit direct current voltage to one of the star-shaped wheels and the means of transmitting voltage from the other of the star-shaped wheels include conductive swivels providing rotatable electrical connections to each of the two star-shaped wheels.

5. The device of claim 1, and wherein the readout is scaled to read
10% for voltage readings returning between 9.91 and 9.78,
12% for voltage readings returning between 9.77 and 9.60,
14% for voltage readings returning between 9.59 and 8.00,
16% for voltage readings returning between 7.99 and 7.00,
18% for voltage readings returning between 6.99 and 5.50,
20% for voltage readings returning between 5.49 and 4.00,
22% for voltage readings returning between 3.99 and 2.75,
24% for voltage readings returning between 2.74 and 2.00,
26% for voltage readings returning between 1.99 and 1.80,
28% for voltage readings returning between 1.79 and 1.60,
30% for voltage readings returning between 1.59 and 1.30,
32% for voltage readings returning between 1.29 and 1.20, and
34% for voltage readings returning between 1.19 and 1.10, when direct current voltage is supplied at about 10 volts.

6. A sensor device for use in measuring moisture in moving compressed hay, such as hay being baled in a hay baler, comprising:

a rotatable penetrating projection mounted adjacent to the moving compressed hay, driven by the moving compressed hay, such that the rotatable penetrating projection serves to provide a moving electrode surface situated within and in electrical contact with the moving compressed hay;

a second electrode surface situated in electrical contact with the moving compressed hay, the second electrode surface spaced apart from the moving electrode surface provided by the rotatable penetrating projection, with moving compressed hay being interposed between the moving electrode surface and the second electrode surface, the interposed moving compressed hay providing an electrical path between the rotatable penetrating electrode surface and the second electrode surface, the conductive quality of the electrical path through the interposed moving compressed hay being a function of the moisture content of the interposed moving compressed hay.

7. The sensor device of claim 6, and wherein the second electrode surface includes a second rotatable penetrating projection mounted adjacent to the moving compressed hay, such that the second rotatable penetrating projection serves as a second moving electrode surface situated within and in electrical contact with the moving compressed hay.

8. The sensor device of claim 7 and wherein the rotatable penetrating projection is one of a plurality of penetrating projections carried by a star-shaped wheel, the star-shaped wheel rotatable about an axis situated transverse to the moving compressed hay and offset from the moving compressed hay, such that the star-shaped wheel is driven to rotate by the moving compressed hay acting upon the penetrating projections.

9. The sensor device of claim 8 and wherein the device includes a pair of star-shaped wheels, with one of the star-shaped wheels providing the plurality of rotatable penetrating projections sequentially forming a first moving electrode surface and the second star-shaped wheel forming a second plurality of moving electrode surfaces, such that the electrode surfaces are not statically positioned relative to the moving compressed hay.

10. The sensor device of claim 9 and wherein the pair of star-shaped wheels are coaxial and further wherein the star-shaped wheels are insulated from each other and from any conductive materials defining a pathway for the moving compressed hay.

11. The sensor device of claim 6 and wherein the compressed moving hay is formed in a rectangular block mass.

12. The sensor device of claim 11 and wherein the compressed moving hay in a rectangular block mass has a linear path and has stems of the hay situated generally transverse to the linear path and parallel to the axis of rotation of the rotatable penetrating projection.

13. The sensor device of claim 6 and wherein the compressed moving hay is formed into a cylinder mass.

14. The sensor device of claim 13 and wherein the cylinder mass is spirally wound about a cylinder axis, the cylinder axis situated parallel to and offset from the axis of rotation of the rotatable penetrating projection.

15. A method of measuring hay moisture within compressed moving hay, the method comprising the steps of:

providing a rotatable penetrating electrode surface within the moving compressed hay and driven by the moving compressed hay;

providing a second electrode surface situated in electrical contact with the moving compressed hay, the second electrode surface spaced apart from the rotatable penetrating electrode surface, with moving compressed hay being interposed between the rotatable penetrating electrode surface and the second electrode surface, the interposed moving compressed hay providing an electrical path between the rotatable penetrating electrode surface and the second electrode surface, providing an electrical current to the rotatable penetrating electrode surface;

detecting the fraction of electrical current conducted through the interposed compressed moving hay; and converting the fraction of electrical current conducted through the interposed compressed moving hay into a moisture reading.

16. The method of claim 15 and wherein the rotatable penetrating electrode surface is one of a plurality of rotatable penetrating electrode surfaces provided by a star-shaped wheel, mounted on a shaft offset from and transverse to the moving compressed hay.

* * * * *